(12) United States Patent
McCarthy (10) Patent No.: US 6,858,039 B2
(45) Date of Patent: Feb. 22, 2005

(54) MITRAL VALVE ANNULOPLASTY RING HAVING A POSTERIOR BOW

(75) Inventor: Patrick McCarthy, Cleveland, OH (US)

(73) Assignee: Edwards Lifesciences Corporation, Irvine, CA (US)

( * ) Notice: Subject to any disclaimer, the term of this patent is extended or adjusted under 35 U.S.C. 154(b) by 92 days.

(21) Appl. No.: 10/192,516

(22) Filed: Jul. 8, 2002

(65) Prior Publication Data

US 2004/0006384 A1 Jan. 8, 2004

(51) Int. Cl.$^7$ .................................................. A61F 2/06
(52) U.S. Cl. ..................................... 623/2.36; 623/2.37
(58) Field of Search ............................... 623/2.36–2.37

(56) References Cited

U.S. PATENT DOCUMENTS

| | | | |
|---|---|---|---|
| 4,055,861 A | 11/1977 | Carpentier et al. | |
| 5,104,407 A | 4/1992 | Lam et al. | |
| 5,258,021 A | 11/1993 | Duran | |
| 5,306,296 A | 4/1994 | Wright et al. | |
| 5,450,860 A | 9/1995 | O'Connor | |
| 5,607,471 A | 3/1997 | Seguin et al. | |
| 6,183,512 B1 | 2/2001 | Howanec, Jr. et al. | |
| 6,187,040 B1 | 2/2001 | Wright | |
| 6,231,602 B1 | 5/2001 | Carpentier et al. | |
| 6,250,308 B1 | 6/2001 | Cox | |
| 6,258,122 B1 | 7/2001 | Tweden et al. | |
| 2001/0034551 A1 | 10/2001 | Cox | |
| 2002/0173844 A1 | 11/2002 | Alfieri et al. | |
| 2003/0083742 A1 * | 5/2003 | Spence et al. ............. | 623/2.16 |

FOREIGN PATENT DOCUMENTS

| | | |
|---|---|---|
| EP | 0 595 791 | 5/1994 |
| EP | 0 860 151 | 8/1998 |
| EP | 1 034 753 A1 | 9/2000 |
| EP | 1 034 753 | 9/2000 |
| FR | 2 708 458 | 8/1993 |
| WO | WO 95/03757 | 2/1995 |
| WO | WO 01/19292 | 3/2001 |
| WO | WO 01/87191 | 11/2001 |
| WO | WO 02/03892 | 1/2002 |

OTHER PUBLICATIONS

IMR Redux—To Repair or Replace, Journal of Thoracic & Cardiovascular Surgery, Aug. 18, 2001.
Effect of Papillary Muscle Position on Mitral Valve Function: Relationship to Homografts, The Society of Thoracic Surgeons Richard P. Cochran et al., 1998.
IA Smolens et al., "Mitral Valve Repair in Heart Failure," The European Journal of Heart Failure 2, (2000), pp 365–371.
Bolling, Steven F., MD, "Mitral Valve Reconstruction In The Patient With Heart Failure," Heart Failure Reviews, 6, 177–185, 2001.

(List continued on next page.)

*Primary Examiner*—Thomas C. Barrett
(74) *Attorney, Agent, or Firm*—David Hauser; Guy L. Cumberbatch (57) ABSTRACT

A mitral heart valve annuloplasty ring having a posterior bow that conforms to an abnormal posterior aspect of the mitral annulus. The ring may be generally oval having a major axis and a minor axis, wherein the posterior bow may be centered along the minor axis or offset in a posterior section. The ring may be substantially planar, or may include upward bows on either side of the posterior bow. The ring may include a ring body surrounded by a suture-permeable fabric sheath, and the ring body may be formed of a plurality of concentric ring elements. The ring is semi-rigid and the posterior bow is stiff enough to withstand deformation once implanted and subjected to normal physiologic stresses. The ring elements may be bands of semi-rigid material. A method of repairing an abnormal mitral heart valve annulus having a depressed posterior aspect includes providing a ring with a posterior bow and implanting the ring to support the annulus without unduly stressing the attachment sutures.

23 Claims, 7 Drawing Sheets

OTHER PUBLICATIONS

Atrioventricular Valve Repair Using Externally Adjustable Flexible Rings, The Journal of Thoracic and Cardiovascular pp. 1333–1337, surgery, Nov. 1995.

The Annals of Thoracic Surgery, pp. 368–369, vol. 46, No. 3, Sep. 1988.

Mitral Valve Reconstruction in the Patient with Heart Failure, Steven F. Bolling, Heart Failure Reviews, 6, 177–185, 2001.

Surgical Alternatives for Heart Failure, The Journal of Heart and Lung Transplant, Steven Bolling et al., 20, 729–733, 2001.

Mitral Valve Repair in Heart Failure, European Journal of Heart Failure, Iva A. Smolens et al., 365–371, 2000.

* cited by examiner

MITRAL VALVE ANNULOPLASTY RING HAVING A POSTERIOR BOW

FIELD OF THE INVENTION

The present invention relates generally to medical devices, specifically to an annuloplasty ring and related procedure for surgically reconstructing the mitral valve annulus of a patient's heart. More specifically, this invention relates to a mitral valve repair device and corresponding technique that conforms to an abnormal annulus in the pathology encountered with functional mitral regurgitation having a posterior aspect depressed below the anterior aspect.

BACKGROUND OF THE INVENTION

In the anatomy of the human heart, the left atrium receives oxygenated blood from the lungs through the pulmonary vein. The mitral valve separates the left atrium from the left ventricle. During diastole, as the contraction triggered by the sinoatrial node progresses through the atria, oxygenated blood passes through the mitral valve into the left ventricle. In this phase, the aortic valve leading into the ascending aorta closes, allowing the left ventricle to fill with blood. A similar flow of venous blood occurs from the right atrium through the pulmonary valve to the right ventricle. Once the ventricles are full, they contract during the systolic phase and pump blood out of the heart. During systole, the mitral valve closes and the aortic valve opens, thus preventing blood from regurgitating into the left atrium and forcing blood into the aorta, and from there throughout the body. Because of the high pressures associated with the left ventricle during systole, proper functioning of the mitral valve to prevent blood from flowing back through the system is extremely important.

Figure 1:
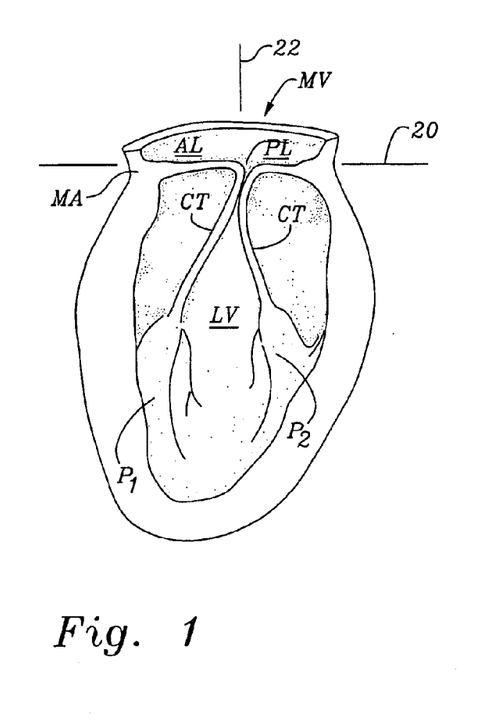
FIG. 1 is a cross-section of a healthy left ventricle through the mitral valve between the anterior and posterior leaflets.
Figure 3:
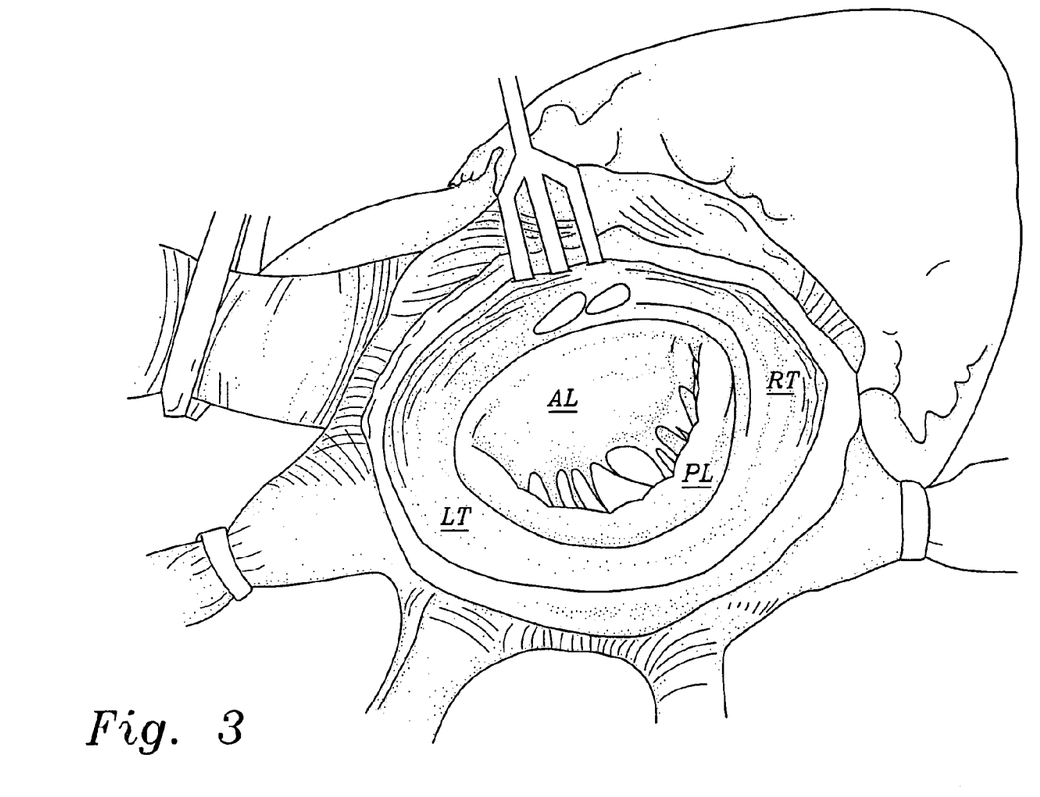
FIG. 3 is an atrial view of the mitral valve of FIG. 2 exposed during a surgical procedure.

The various anatomical components of the left ventricle LV and mitral valve MV are depicted in FIG. 1 as seen in vertical cross-section along an anterior-posterior plane. The mitral annulus MA comprises a fibrous ring encircling the orifice between the left atrium LA and the left ventricle LV. The average human mitral annular cross-sectional area is 5–11 cm$^2$. The anterior aspect of the mitral annulus MA forms a part of the "cardiac skeleton" and includes left and right fibrous trigones, LT and RT. FIG. 3 illustrates the mitral valve from the left atrium as exposed during surgery. The mitral valve is a bicuspid valve having a posterior leaflet PL that cooperates with an anterior leaflet AL. The left trigone LT and right trigone RT are indicated at the junction points of the anterior leaflet AL and posterior leaflet PL. These junction points are also known as commissures between the leaflets. The posterior aspect of the mitral annulus MA, in contrast to the anterior aspect, consists mainly of muscular tissue of the outer wall of the heart.

With reference again to FIG. 1, a pair of papillary muscles $P_1$ and $P_2$ attach to the lower portion of the interior wall of the left ventricle LV. Chordae tendineae CT extend between and link the papillary muscles $P_1$ and $P_2$ and free edges of the anterior and posterior leaflets AL and PL. The chordae tendineae are string-like in appearance and are sometimes referred to as "heart strings." Although not shown in the drawing, chordae tendoneae CT extend between each of the papillary muscles $P_1$ and $P_2$ and both leaflets. Contraction of the papillary muscles $P_1$ and $P_2$ pulls the chordae tendoneae CT, which in turn pull the leaflets open, and when the muscles relax the chordae tendonae become slack, allowing the leaflets to come together or "coapt." As seen in FIG. 1, the leaflets coapt along a substantial surface area in the normal functioning heart, with the free edges of the leaflets mutually bending toward the left ventricle LV.

As seen in FIG. 1, and for purpose of discussion, the mitral annulus MA of a normal, healthy heart lies generally in a datum plane 20 defined perpendicular to the average blood flow direction 22 through the mitral valve MV. Although a typical mitral annulus MA may be three-dimensional, the datum plane 20 is representative of the relative positions of the anterior and posterior side of the annulus.

In many developed countries, congestive heart failure is a leading cause of hospitalization and death, and its incidence is increasing. When imperfections in the mitral valve allows blood to flow backward into the left atrium, known as secondary mitral regurgitation, the left ventricle must pump progressively harder to circulate blood throughout the body, which in turn promotes congestive heart failure. Heart transplantation is considered a standard treatment for select patients with severe congestive heart failure and end-stage heart disease, but only a small number of donor hearts are available and there are severe surgical risks for weaker patients. Accordingly, alternative medical and surgical strategies are evolving to treat such conditions.

Figure 2:
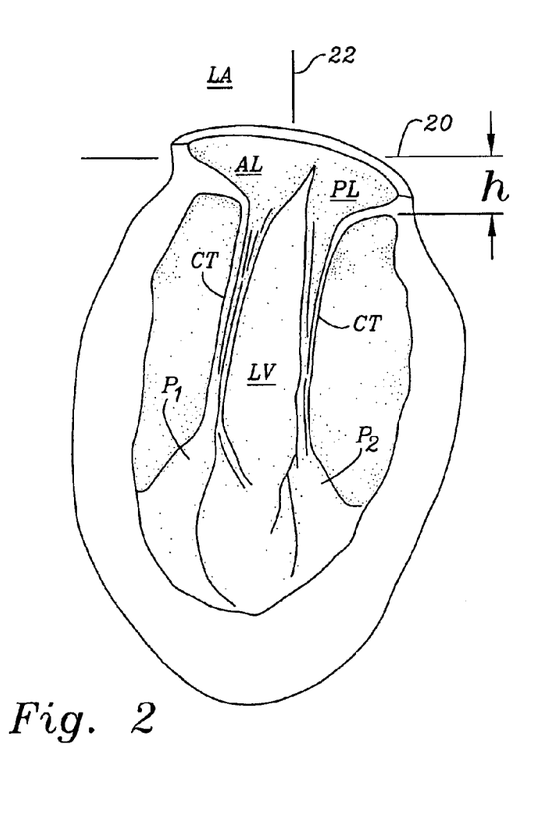
FIG. 2 is a cross-section of a dilated left ventricle through the mitral valve between the anterior and posterior leaflets.

One typical cause of mitral regurgitation is malformation of the mitral annulus MA along the more flexible posterior aspect of the annulus. As seen in FIG. 2, some patients experience a depression h of the posterior aspect of the annulus caused by dilation of the left ventricle LV. Dilation of the left ventricle LV is a symptom associated with mitral regurgitation in patients with iopathic dilated cardiomyopathy or ischemic cardiomyopathy, and in patients with long-standing valvular regurgitation from other etiologies such as myxomatous disease, endocarditis, congenital defects, or rheumatic valvular disease. FIG. 3 illustrates the subsequent loss of coaptation between the posterior and anterior leaflets AL and PL from this posterior aspect depression, as seen from above.

As seen in FIG. 2, dilation of the left ventricle LV generally increases the distance between the papillary muscles $P_1$ and $P_2$ and the mitral annulus MA. This in turn increases the tension in the chordae tendonae CT. The droop or depression of the posterior aspect of the annulus below the datum plane 20 by the distance h in combination with the increased tension in the chordae reduces the ability of the leaflets to come together during systole.

Various interventions have been used to alter the size of the regurgitant orifice area. Annuloplasty rings have been developed in various shapes and configurations over the years to correct mitral regurgitation and other conditions which reduce the functioning of the valve. For example, Carpentier, et al. in U.S. Pat. No. 4,055,861 disclosed two semi-rigid supports for heart valves, one of which being closed (or D-shaped) and the other being open (or C-shaped). In the closed configuration, the ring is generally symmetric about an anterior-posterior plane, and has a convex posterior side and a generally straight anterior side. U.S. Pat. Nos. 5,104,407, 5,201,880, and 5,607,471 all disclose closed annuloplasty rings that are bowed slightly upward on their anterior side. Because the anterior aspect of the mitral annulus MA is fibrous and thus relatively inflexible (at least in comparison to the posterior aspect), the upward curve in the anterior side of each ring conforms that ring more closely to the anatomical contour of the mitral annulus, and thus reduces undue deformation of the annulus.

In general, conventional annuloplasty rings are intended to restore the original configuration of the mitral annulus MA, or in other words bring the annulus as close as possible back to the datum plane 20 as seen in FIG. 1. When correcting a condition as seen in FIG. 2, high stresses are created in the sutures connecting the annuloplasty ring to posterior aspect of the annulus because the ring "pulls" the annulus upward. The stresses sometimes result in the dehiscence or separation of the ring from the annulus at this location because the sutures pull through the tissue.

It should be noted here that correction of the aortic annulus requires a much different ring then with a mitral annulus. For example, U.S. Pat. Nos. 5,258,021 and 6,231,602 disclose sinusoidal or so-called "scalloped" annuloplasty rings that follow the up-and-down shape of the three cusp aortic annulus. Such rings would not be suitable for correcting a mitral valve deficiency.

While good results in the treatment of congestive heart failure and mitral regurgitation have been obtained in the preliminary applications of the above-described methods and apparatuses, it is believed that these results can be significantly improved. Specifically, it would be desirable to produce a mitral annuloplasty ring that can reduce stresses associated with the implantation of conventional rings.

SUMMARY OF THE INVENTION

The present invention provides an annuloplasty ring for implantation in a mitral valve annulus that has a pathologic condition such that the posterior aspect thereof droops downward abnormally. The annuloplasty ring includes a rounded ring body having an anterior section and a posterior section. The ring body is oriented about a central flow axis that defines an upward direction and a downward direction, the downward direction corresponding to the direction of blood flow through the mitral valve annulus. The posterior section the ring body bows downward out of a plane perpendicular to the central flow axis.

The ring body may bow downward between about 2–15 mm from one end thereof to a lowest point, and desirably bows downward between about 4–8 mm from one end thereof to a lowest point. The bow in the ring body may or may not be centered in the posterior section. Preferably, the ring body is made of a malleable material such that the bow in the ring body may be manually reshaped. Desirably, the ring body is made of a semi-rigid material that will retain its posterior bow in opposition to the stresses that will be imparted by muscles of the heart throughout each beating cycle. The ring body may be substantially planar except in the posterior section, or an anterior section of the ring body may bow upward from one end thereof to a lowest point.

In plan view, as seen along the flow axis, the ring body preferably defines an oval shape with a major axis perpendicular to a minor axis, the minor axis bisecting both the anterior and posterior sections. Further, the bow in the posterior section may begin at symmetric locations across the minor axis that are spaced from the major axis around the ring body by an angle θ of between about 0–45°, more preferably about 30°.

The ring body may further include two upward bows on either side of the downward bow on the posterior section, and wherein downward bow may be between about 2–15 mm. In one embodiment, the ring body comprises a plurality of ring elements concentrically disposed. A polymer strip in between each ring element may be provided. Optionally, the ring elements comprise bands that have a substantially larger height in the flow axis dimension than in the dimension perpendicular to the flow axis. Further, the ring elements may have varying heights so that the ring body is more flexible in the posterior section than around the remainder of the ring body.

Another aspect of the present invention is a method of repairing a mitral heart valve annulus that has a posterior aspect that is depressed downward along the blood flow axis relative to an anterior aspect. The method includes implanting an annuloplasty ring having an anterior section sized to fit the anterior aspect of the annulus and a posterior section sized to the posterior aspect, wherein the ring posterior section bows downward parallel to the central axis relative to the anterior section. The annuloplasty ring may be malleable and the surgeon adjusts the bow in the posterior section manually.

Another aspect of the invention is a method of repairing a mitral heart valve annulus that has a posterior aspect, an anterior aspect, and a blood flow axis. The method includes inspecting the shape of the mitral annulus and selecting a three-dimensional annuloplasty ring based on the shape of the mitral annulus. The selected annuloplasty ring has an anterior section and a posterior section generally arranged around a central axis. The central axis defines an upward direction and a downward direction, wherein the ring posterior section bows downward out of a plane perpendicular to the central axis. The method includes implanting the annuloplasty ring so that the ring posterior section attaches to the posterior aspect of the mitral valve annulus and the posterior section bows in the blood flow direction.

DESCRIPTION OF THE PREFERRED EMBODIMENTS

The attached figures illustrate several exemplary embodiments of the annuloplasty ring of the present invention, which can be described as being continuous and having an anterior side, a posterior side and right and left sides. All of the sides are generally curvilinear with no specific demarcations to indicate abrupt transitions therebetween. Rather, smooth transitional sections between the adjacent sides provide curvilinear connections that give the ring a generally rounded (e.g., oval) configuration.

Figure 4:
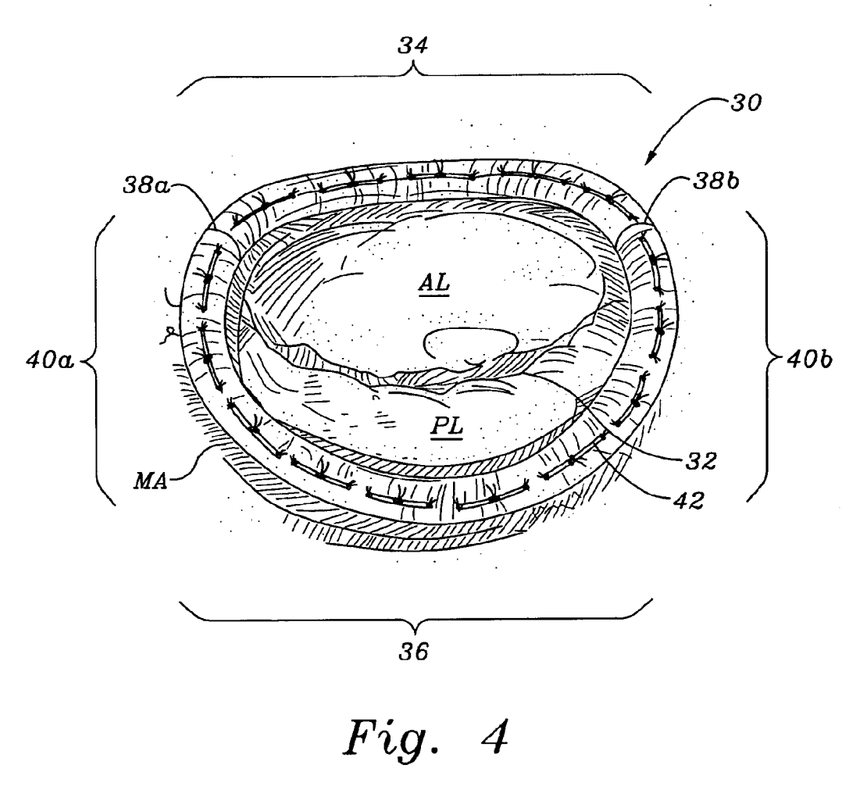
FIG. 4 is a plan view of annuloplasty ring of the present invention implanted so as to restore competency to the mitral valve.

An exemplary annuloplasty ring 30 of the present invention is shown in FIG. 4 implanted around a mitral annulus MA. As described above, the mitral annulus has an anterior leaflet AL and a posterior leaflet PL. When the ring 30 is implanted, the leaflets are brought closer together and supported so that they meet at a coaptation surface 32. The ring 30 thus corrects the problem of functional mitral regurgitation.

The ring 30 has an oval or somewhat D-shaped configuration with a relatively straight anterior section 34 opposite a curved posterior section 36. A pair of trigone or commissure markers 38a, 38b generally delimit the anterior side 34, while a pair of opposed side sections 40a, 40b extend between each of these markers and the posterior section 36. A plurality of knotted suture loops 42 are typically used to secure the ring 30 to the mitral annulus MA, although other fasteners such as staples, fibrin glue, or the like may be used.

In the pathological conditions for which the annuloplasty ring 30 is best suited, the posterior aspect of the mitral annulus is depressed relative to the anterior aspect, as is illustrated in FIG. 2. In the view of FIG. 4, the posterior aspect will be depressed into the page relative to the anterior aspect. The annuloplasty ring 30 of the present invention has a shaped posterior section 36 that generally follows the modified shape of the mitral annulus MA. In other words, the posterior section 36 is bowed into the page relative to the anterior section 34. When secured in place with sutures 42, for example, the ring 30 supports the mitral annulus MA in its modified shape, rather than trying to revert the annulus back to the original substantially planar configuration. At the same time, the ring 30 desirably constricts the orifice circumference defined by the annulus so as to bring the anterior leaflet AL and posterior leaflet PL closer together. Because the ring 30 does not pull the posterior aspect of the mitral annulus MA upward from its modified position, high stresses are not set up in the attachment sutures 42 and thus there is less potential for the dehiscence.

Figure 5:
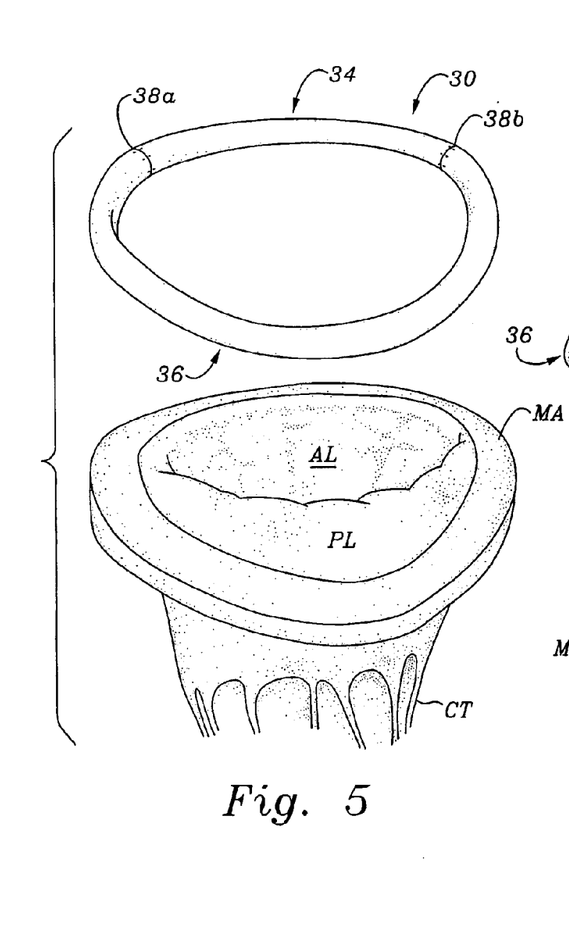
FIG. 5 is a perspective view of an annuloplasty ring of the present invention over an abnormal mitral valve as viewed from the posterior side.
Figure 6:
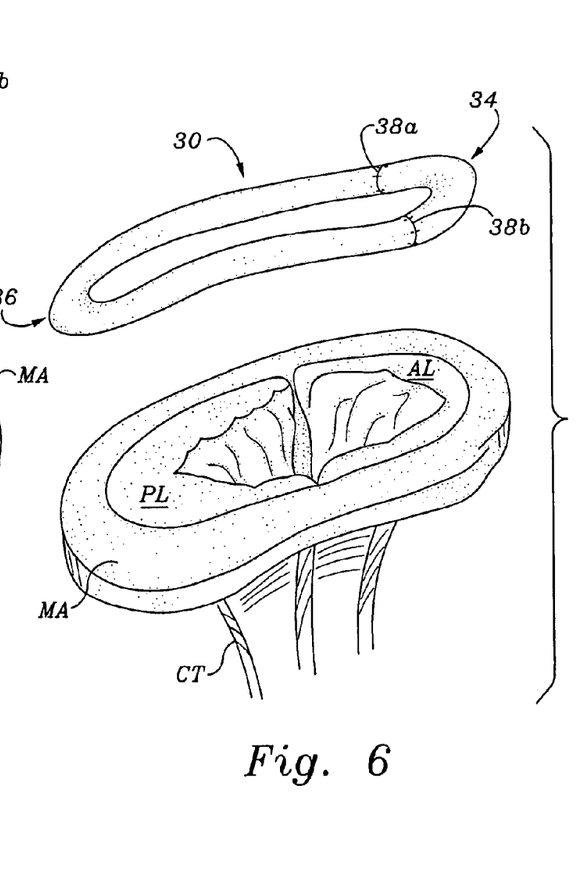
FIG. 6 is a perspective view of the annuloplasty ring of FIG. 5 over the abnormal mitral valve as seen from the side.

FIGS. 5 and 6 illustrate the exemplary annuloplasty ring 30 in perspective above a mitral annulus that is depressed on its posterior side. The bow of the ring 30 in its posterior section 36 is seen best in FIG. 6 mimicking the depression of the posterior aspect of the mitral annulus MA in the pathology encountered with functional mitral regurgitation.

Figures 7A, 7B, 7C:
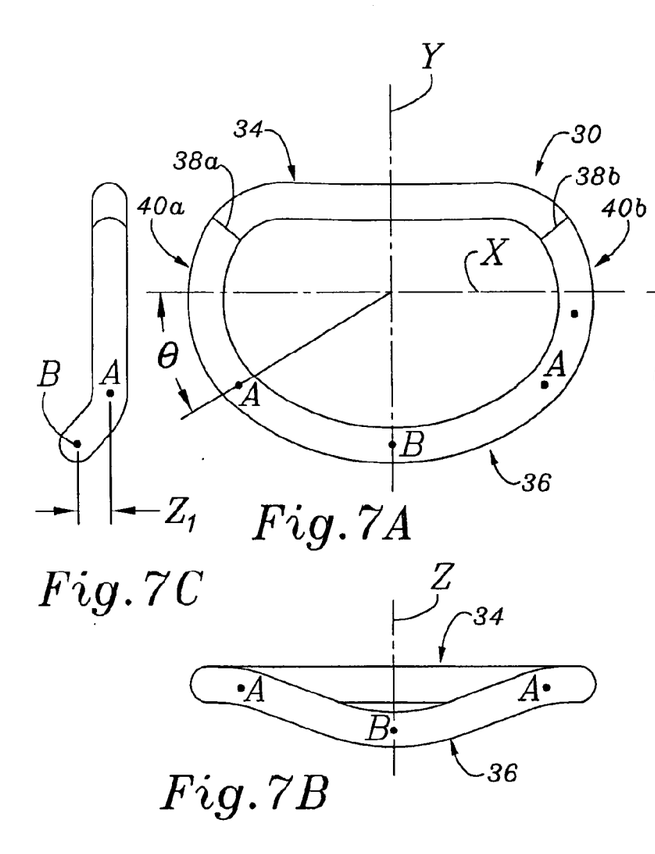
FIGS. 7A–7C are plan, front, and side views of an exemplary annuloplasty ring of the present invention having a posterior bow.

The exemplary annuloplasty ring 30 of FIGS. 4–6 is shown in more detail in FIGS. 7A–7C. The ring 30 is shown complete with a fabric covering. For purpose of orientation, FIG. 7A illustrates orthogonal axes wherein the X- and Y-axes generally define the datum plane 20 as mentioned above with respect to FIGS. 1 and 2. The X-axis extends across the ring 30 from one side 40a to the opposite side 40b at the point of maximum dimension. The X-axis thus defines a major axis of the ring 30. The Y-axis defines a plane of symmetry for the ring 30 extending between a midpoint of the anterior side 34 to a midpoint of the posterior section 36. The Y-axis also defines a minor axis for the ring 30.

As with many conventional rings, the ratio of the minor axis dimension to the major axis dimension is desirably about 3:4. This size ratio is the "classic" shape of the mitral annulus, and may be the best configuration of the annuloplasty ring 30. However, it is contemplated that other shapes that have smaller minor axis-to-major axis ratios may actually increase leaflet coaptation. Although not geometrically precise, the non-circular ring configuration may be considered oval, elliptical or D-shaped. It should be noted that the present invention could also take the form of a discontinuous ring that has a C-shape, for example. The break in such a ring may be in the anterior section, and the posterior section is continuous and exhibits the downward bow as explained.

The Z-axis in FIG. 7B lies along of the axis of blood flow through the ring 30 when implanted, and it will be understood that the positive Z direction is the "upward" direction, the negative Z direction is the "downward" direction, and the ring 30 is designed to be implanted in a mitral annulus such that blood will flow in the downward direction.

Figures 8A, 8B, 8C:
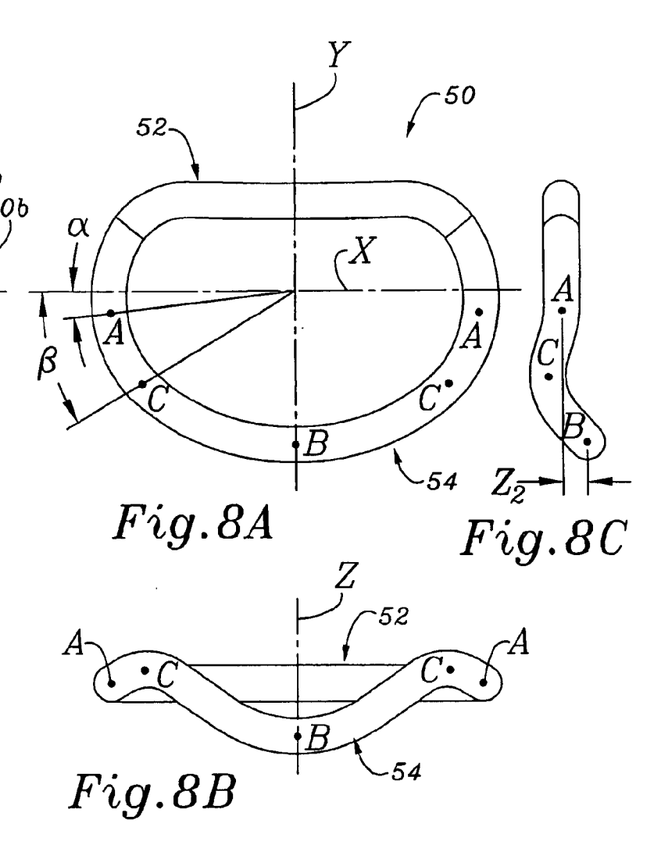
FIGS. 8A–8C are plan, front, and side views of an alternative annuloplasty ring of the present invention having a posterior bow between two raised portions.

Several points are noted around the ring 30 to help describe the posterior bow. These points, and the ones shown in FIGS. 8A–8B, are imaginary center points through the cross-section of the ring 30. Two points A are symmetrically located on either side of the Y-axis at an angular distance θ from the X-axis. The midpoint of the posterior section 36 is denoted B. The ring 30 has a posterior bow such that the point B is at the lowest elevation along the Z-axis. The magnitude of this posterior bow is indicated by the dimension $Z_1$ in FIG. 7C. The points A on either side of the posterior section 36 represent the location where the posterior bow begins. That is, except for the posterior section, the ring 30 is preferably substantially planar. However, the anterior section 34 can optionally be bowed upward by a distance of between about 2–4 mm (0.08–0.16 inches), as in certain rings of the prior art. In the latter example, the posterior section 36 bows downward in the Z-direction relative to the elevation of the trigone markers 38a, 38b.

Various possible configurations for the ring 30 as seen in FIGS. 7A–7C are contemplated, with the dimension $Z_1$ and the angle θ varying between ranges determined by the overall size of the mitral annulus, the extent of anatomical droop of the posterior aspect, and various other factors including surgeon preference. Nevertheless, certain ranges are believed suitable to support and correct a majority of the patients exhibiting the particular anatomical irregularity as described herein. The downward bow or posterior bow preferably extends along a majority of the posterior section 36 between the points A, which points are between 0 and 45° from the X-axis (θ). More preferably, the points A are between 20–40°, and more particularly about 30° from the X-axis. The magnitude of bow $Z_1$ may be between about 2–15 mm (0.08–0.59 inches), and more typically is between about 4–8 mm (0.16–0.31 inches), depending on the size of the ring.

Although the ring 30 is shown in FIGS. 7A–7C as symmetric about the Y-axis, it does not necessarily have to be so. For example, the point B may be displaced from the Y-axis such that the downward bow is not centered in the posterior section 36. An asymmetric ring is shown and described below with reference to FIGS. 9A and 9B.

FIGS. 8A–8C illustrate an alternative annuloplasty ring 50 of the present invention that has both upward and downward bows. Again, the ring 50 is shown complete with a fabric covering. The ring 50 includes an anterior section 52, a posterior section 54, and a pair of side sections (not numbered) therebetween. The ring 50 is generally planar on the anterior section 52 and shaped on the posterior section 54. The points A symmetrically disposed across the Y-axis again denote the locations on each side where the ring 50 begins to curve out of a plane. In this embodiment, the ring curves upward in the Z-direction from the points A, as best seen in FIG. 8B, to high points C, and then dips downward to the midpoint B of the posterior section 54. The downward bow of the ring between points A and B is shown in FIG. 8C as the dimension $Z_2$, which has a magnitude similar to that given for $Z_1$ in FIG. 7C. The upward curve may be selected so as to better match the patient's annulus shape. Furthermore, the anterior section 52 may be upwardly bowed by a distance of between about 2–4 mm (0.08–0.16 inches).

Various permutations of the ring 50 shown in FIGS. 8A–8C are contemplated, with the dimensions being altered based on numerous factors. In an exemplary embodiment, the points A are desirably disposed an angular distance α from the X-axis of between about 0–15°, and more desirably between about 5–10°. The points C of maximum height of the ring 50 are preferably spaced an angular distance β from the X-axis of between about 15–45°, and more preferably between about 25–35°. The lowest point B of the ring 50 may be bowed along the Z-axis as in the embodiment of FIGS. 7A–7C, so that, as indicated FIG. 8C, $Z_2$ is desirably between about 2–15 mm (0.08–0.59 inches), and more typically is between about 4–8 mm (0.16–0.31 inches), depending on the size of the ring. Therefore, the total height of the ring 50 is at least 2 mm, and may be greater than 15 mm.

Figure 9A:
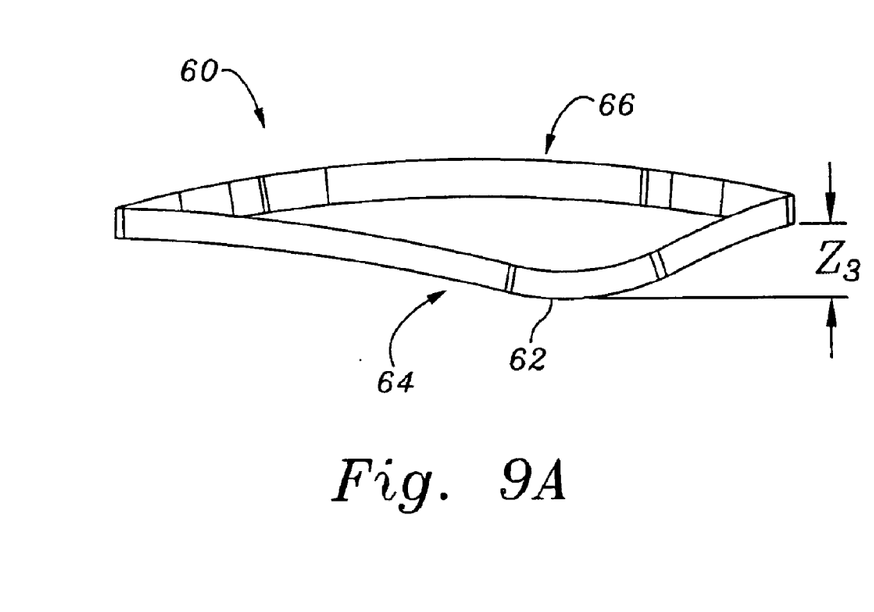
FIGS. 9A and 9B are front and side elevational views, respectively, of an inner ring body of a further annuloplasty ring of the present invention having an off-center posterior bow and an anterior bow.
Figure 9B:
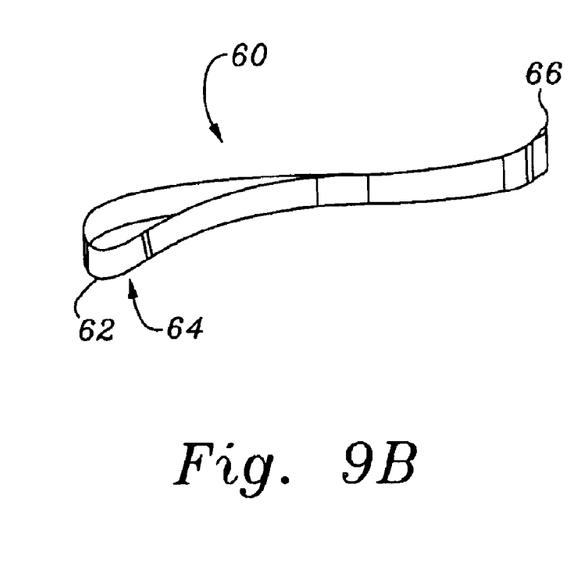

FIGS. 9A and 9B show an inner ring body 60 for use in an annuloplasty ring of the present invention. The ring body 60 has a posterior bow 62 that is offset from the center of a posterior section 64. In the illustrated embodiment, the bow 62 is offset toward the posterio-medial side (to the right) by about 20% of the entire major axis width of the ring body 60. Another way to state the offset is that, in plan view, the bow 62 is centered at a clock position, with 12:00 being centered in the anterior side. In that sense, the bow 62 is centered between 3:00 and 6:00, and more preferably is centered at about 5:00. The axial bow $Z_3$ is shown and may vary from about 2.0 mm (0.08 inches) to about 4.0 mm (0.16 inches), and more preferably from about 3.0 mm (0.12 inches) to about 3.8 mm (0.15 inches), depending on ring size. In addition, the ring body 60 has an anterior section 66 that is upwardly bowed by a distance of between about 2–4 mm (0.08–0.16 inches).

The inner ring body 60 demonstrates an asymmetric ring that conforms to patients that have a posterior annular bow that is displaced from the midline. It is believed that most patients have such a malformed anatomy resulting from the pathologic conditions described herein. However, posterior bows that are centered or even offset to the left have been observed. Therefore, one configuration of ring that is embodied in the present invention is one that is pre-shaped with a posterior bow in the middle or to the right, and that is malleable so that the bow can be exaggerated or diminished by the surgeon after examination of the precise shape of the patient's annulus. Further, in such a convertible ring the bow can even be displaced, from the right to the left, for example. Although the material of the ring permits manual deformation, it would be stiff enough to withstand further deformation once implanted and subjected to normal physiologic stresses.

The ring preferably includes an inner ring body and an outer sewing sheath that permits the ring body to be sutured into the mitral annulus. The sewing sheath should be sufficiently porous and/or flexible to permit sutures to be passed therethrough. One exemplary construction is to enclose the inner ring body in a tubular sheath of suture-permeable material, such as silicone, which is then covered with a fabric tube, such as polyethyl terapthalate.

As opposed to flexible annuloplasty rings that are designed simply to reduce the circumference of the mitral annulus, the annuloplasty ring of the present invention must be semi-rigid. It must retain its posterior bow in opposition to the stresses that will be imparted by muscles of the heart throughout each beating cycle. For example, the ring body may be made from materials such as Elgiloy (a cobalt-nickel alloy), titanium, or Nitinol (a nickel-titanium alloy).

Figure 10:
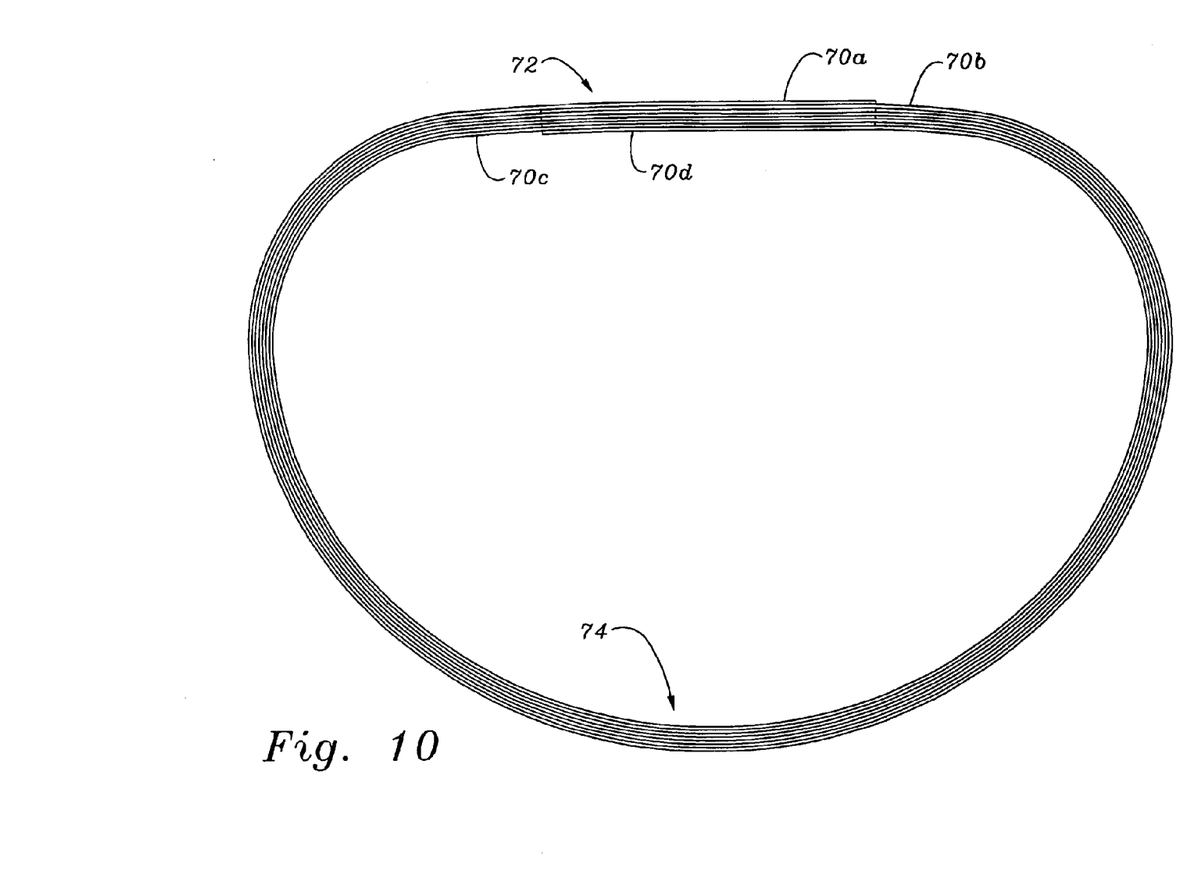
FIG. 10 is a top plan view of an inner ring body of an annuloplasty ring of the present invention showing details of a composite band construction.

FIG. 10 illustrates one exemplary construction of the inner body of the annuloplasty rings of the present invention that utilizes multiple flat bands of Elgiloy in a composite structure. Specifically, there are four bands 70a, 70b, 70c, and 70d from the outside to the inside. The four bands are concentrically disposed in the shape of the ring. Each band is a flat strip of material having a width of between about 1.4–2.0 mm (0.056–0.078 inches). In one embodiment, the bands 70 overlap in the anterior section 72 of the ring body and are fastened together by, for example, spot welding at multiple points. The width of each strip may also be greater in the anterior section 72 than in a posterior section 74, which means that the ring body is more flexible in the posterior section than in any other section. Although not shown, a plurality of strips of protective film is used in between each band 70, and on the outer face of the outer band 70a. The strips may be a polymer such as Mylar. The strips help reduce rubbing between the bands 70 and also deflect suture needles from the outer band 70a and thus prevent scratching thereto.

It will also be readily apparent that supporting the mitral valve annulus with the present annuloplasty ring will maintain the posterior leaflet depressed below the anterior leaflet, and thus the area of coaptation therebetween will be different than in a healthy valve. This is required by the pathology of the ventricle with displacement of the papillary muscles and posterior leaflet. However, those of skill in the art will recognize that this slight realignment of the leaflets is acceptable because of the surplus area of the leaflets available for coaptation, and because the realignment will be offset by other changes to the shape of the annulus that should over time improve coaptation of the two leaflets and therefore decrease regurgitation.

It will also be appreciated by those of skill in the relevant art that various modifications or changes may be made to the examples and embodiments of the invention described in this provisional application, without departing from the intended spirit and scope of the invention. In this regard, the particular embodiments of the invention described herein are to be understood as examples of the broader inventive concept disclosed in this application.

What is claimed is:

1. An annuloplasty ring for implantation in a mitral valve annulus, said annuloplasty ring comprising:

a rounded ring body having an anterior section adapted to be implanted on the anterior aspect of the mitral valve annulus, and a posterior section adapted to be implanted on the posterior aspect of the mitral valva annulus;

wherein the ring body is oriented about a central flow axis, the flow axis defining an upward direction and a downward direction, the downward direction corresponding to the direction of blood flow through the mitral valve annulus; and, wherein in the posterior section the ring body bows downward out of a plane perpendicular to the central flow axis, and wherein the downward bow in off-center in the posterior section and exhibits smooth curvilinear transitions to the adjacent ring body sections.

2. The annuloplasty ring of claim 1, wherein, in the posterior section, the ring body bows downward between about 2–15 mm as measured along the flow axis from a point around the ring body at which the downward bow begins to a lowest point of the downward bow.

3. The annuloplasty ring of claim 2, wherein the ring body bows downward between about 4–8 mm.

4. The annuloplasty ring of claim 1, wherein the bow in the ring body is off-center in the posterior section toward a posterio-medial side of the ring body as viewed from an inflow perspective.

5. The annuloplasty ring of claim 4, wherein in plan view as seen along the flow axis the ring body generally defines an oval shape with a major axis perpendicular to a minor axis, wherein the minor axis bisects both the anterior and posterior sections, and wherein the bow in the posterior section is offset toward the posterio-medial side by about 20% of the entire major axis width of the ring body.

6. The annuloplasty ring of claim 4, wherein in plan view as seen along the flow axis the ring body generally defines an oval shape with a major axis perpendicular to a minor axis, wherein the minor axis bisects both the anterior and posterior sections, and wherein the bow in the posterior section is centered at a clock position, with 12:00 being centered in the anterior side, and the bow is centered between 3:00 and 6:00.

7. The annuloplasty ring of claim 1, wherein the ring body is made of a malleable material such that the bow in the ring body may be manually reshaped.

8. The annuloplasty ring of claim 1, wherein the ring body is made of a semi-rigid material that will retain its posterior bow in opposition to the stresses that will be imparted by muscles of the heart throughout each beating cycle.

9. The annuloplasty ring of claim 1, wherein in the anterior section the ring body bows upward from adjacent trigone markers.

10. The annuloplasty ring of claim 1, wherein the ring body comprises a plurality of ring elements concentrically disposed.

11. The annuloplasty ring of claim 10, further including a polymer strip in between each ring element.

12. The annuloplasty ring of claim 10, wherein the ring elements comprise bands that have a substantially larger height in the flow axis dimension than in the dimension perpendicular to the flow axis.

13. The annuloplasty ring of claim 12, wherein the ring elements have varying heights so that the ring body is more flexible in the posterior section than around the remainder of the ring body.

14. A method of repairing a mitral heart valve annulus that has a posterior aspect that is depressed downward along the blood flow axis relative to an anterior aspect, comprising:
implanting an annuloplasty ring having an anterior section sized to fit the anterior aspect of the annulus and a posterior section sized to the posterior aspect, wherein the ring posterior section bows downward parallel to the central axis relative to the anterior section.

15. The method of claim 14, wherein the annuloplasty ring is malleable and the surgeon adjusts the bow in the posterior section manually.

16. The method of claim 14, wherein the ring posterior section bows downward between about 4–8 mm parallel to the central axis relative to the anterior section.

17. The method of claim 14, wherein the posterior aspect is depressed downward along the blood flow axis off-center in the posterior section and the bow in the ring is similarly off-center in the posterior section.

18. The method of claim 17, wherein the posterior aspect is depressed downward along the blood flow axis toward a posterio-medial side of the mitral annulus and the bow in the ring is similarly off-center in the posterior section toward a posterio-medial side of the ring.

19. The method of claim 14, wherein the ring body is made of a malleable material and the method includes manually reshaping the ring to have the posterior bow.

20. A method of repairing a mitral heart valve annulus that has a downwardly depressed posterior aspect, an anterior aspect, and a blood flow axis, comprising:
inspecting the shape of the mitral annulus;
selecting a three-dimensional annuloplasty ring based on the shape of the mitral annulus, the annuloplasty ring having an anterior section and a posterior section generally arranged around a central axis, the central axis defining an upward direction and a downward direction, wherein the ring posterior section bows downward out of a plane perpendicular to the central axis; and
implanting the annuloplasty ring so that the ring posterior section attaches to the posterior aspect of the mitral valve annulus and the posterior section bows in the blood flow direction.

21. An annuloplasty ring for implantation in a mitral valve annulus, said annuloplasty ring comprising:
a rounded ring body having an anterior section adapted to be implanted on the anterior aspect of the mitral valve annulus and a posterior section adapted to be implanted on the posterior aspect of the mitral valve annulus;
wherein the ring body is oriented about a central flow axis, the flow axis defining an upward direction and a downward direction, the downward direction corresponding to the direction of blood flow through the mitral valve annulus wherein the ring body comprises a plurality of bands concentrically disposed that have a substantially larger height in the flow axis dimension than in the dimension perpendicular to the flow axis, and wherein the bands have varying heights so that the ring body is more flexible in the posterior section than around the remainder of the ring body; and,
wherein in the posterior section the ring body bows downward out of a plane perpendicular to the central flow axis.

22. The annuloplasty ring of claim 21, further including a polymer strip in between each ring element.

23. The annuloplasty ring of claim 21, wherein the bands overlap in the anterior section of the ring body and are fastened together at multiple points.

* * * * *